(12) United States Patent
Yudkovitch et al.

(10) Patent No.: US 7,997,269 B2
(45) Date of Patent: Aug. 16, 2011

(54) SYSTEM AND METHOD OF SAFELY DISPLAYING PK/PD ANESTHETIC DRUG MODELS

(75) Inventors: Laurence Yudkovitch, Mequon, WI (US); Ronald P. Makin, Fitchburg, WI (US); René Coffeng, Helinski (FI); Michael Mitton, Sun Prairie, WI (US)

(73) Assignee: General Electric Company, Schenectady, NY (US)

( * ) Notice: Subject to any disclaimer, the term of this patent is extended or adjusted under 35 U.S.C. 154(b) by 1050 days.

(21) Appl. No.: 11/619,870

(22) Filed: Jan. 4, 2007

(65) Prior Publication Data
US 2008/0097166 A1  Apr. 24, 2008

Related U.S. Application Data

(60) Provisional application No. 60/829,968, filed on Oct. 18, 2006.

(51) Int. Cl.
*A61M 16/00* (2006.01)
*G06F 3/00* (2006.01)

(52) U.S. Cl. ......... 128/203.14; 128/203.12; 128/203.13; 128/203.25; 128/204.18; 128/204.21; 128/204.22; 128/204.26; 128/205.23

(58) Field of Classification Search ............. 128/203.12, 128/203.13, 203.14, 203.25, 200.24, 205.23, 128/204.18, 204.21, 204.22, 204.23, 920, 128/922, 923, 924; 702/19; 703/11, 12; 600/300; 715/200, 249, 273, 700, 764, 765
See application file for complete search history.

(56) References Cited

U.S. PATENT DOCUMENTS

| 6,937,257 | B1 * | 8/2005 | Dunlavey ..................... 715/763 |
| 7,693,697 | B2 | 4/2010 | Westenskow et al. |
| 2003/0156143 | A1 | 8/2003 | Westenskow |
| 2006/0081244 | A1 * | 4/2006 | Bouillon et al. ......... 128/200.24 |
| 2008/0033661 | A1 * | 2/2008 | Syroid et al. .................... 702/22 |
| 2008/0108970 | A1 | 5/2008 | Viertio-Oja |

FOREIGN PATENT DOCUMENTS
WO  WO 02/32036  4/2002

OTHER PUBLICATIONS

Gurushanthaiah et al., Visual Display Format Affects the Ability of Anesthesiologists to Detect Acute Physiologic Changes: A Laboratory Study Employing a Clinical Display Simulator. Anesthesiology. 83(6):1184-1193, Dec. 1995.*

(Continued)

*Primary Examiner* — Justine R Yu
*Assistant Examiner* — Clinton Ostrup
(74) *Attorney, Agent, or Firm* — Andrus, Sceales, Starke & Sawall, LLP (57) ABSTRACT

The system and method includes a treatment device such as an anesthetic machine or IV, a monitor and a display configured to display real-time PK/PD data associated with an anesthetic agent administered to the patient. The system and method further includes a safety control means configured to control the display such that one of a basic display state, an interactive effects display state, and a display inhibited state is selected and displayed according to the anesthetic agents and levels of the same being administered to the patient.

14 Claims, 7 Drawing Sheets

OTHER PUBLICATIONS

Drews et al., Drug Delivery as Control Task: Improving Performance in a Common Anesthetic Task., Human Factors: The Journal of the Human Factors and Ergonomics Society, vol. 48, No. 1, 85-94, Spring 2006.*

Syroid et al., Development and evaluation of a graphical anesthesia drug display., Anesthesiology; 96 (3); 565-75, Mar. 2002.*

Kennedy et al., The effect of a model-based predictive display on the control of end-tidal sevoflurane concentrations during low-flow anesthesia., Anesth Analg. 99 (4): 1159-63, Oct. 2004.*

McGuire (Example User Interfaces for Various Caregivers; Copyright 2000, http://www.uprforum.com/Chap12.htm, p. 1-59).

Office Action dated Aug. 17, 2010.

Minto et al., "Response Surface Model for Anesthetic Drug Interactions", Anesthesiology, 2000, 92:1603-1616.

Parker et al., "Control-relevant modeling in drug delivery", Advanced Drug Delivery Reviews, 2001, 48:211-228.

Short et al., "Hypnotic and Anaesthetic Interactions Between Midazolam, Propofol and Alfentanil", British Journal of Anaesthesia, 1992, 69:162-167.

Vuyk et al., "Pharmacokinetic and Pharmacodynamic Interactions Between Opioids and Propofol", Journal of Clinical Anesthesia, 1997, 9:23S-26S.

Office Action issued Apr. 19, 2011, for U.S. Appl. No. 11/564,005.

* cited by examiner

SYSTEM AND METHOD OF SAFELY DISPLAYING PK/PD ANESTHETIC DRUG MODELS

CROSS REFERENCE TO RELATED APPLICATIONS

This application claims priority under 35 U.S.C. §119(e) of the U.S. Provisional Application No. 60/829,968, filed on Oct. 18, 2006 and entitled "SYSTEM AND METHOD OF SAFELY DISPLAYING PK/PD ANESTHETIC DRUG MODELS."

FIELD OF THE DISCLOSURE

The present disclosure is related to the field of clinical systems. More particularly, the present disclosure is related to the filed of anesthetic drug model displays.

BACKGROUND OF THE DISCLOSURE

In an operating room, the anesthesiologist needs to assess the patient's condition and adjust the therapy using a wide variety of distinct medical devices. These devices often don't talk to each other, and hence only provide one piece of the picture. Clinicians have to mentally keep track of the patient's level of sedation, analgesia and relaxation based on the amount of drugs they've administered, and their familiarity with the drug's pharmacokinetic/pharmacodynamic (PK/PD) models.

The practice of intra-operative anesthesia typically involves administering sedative, analgesic and neuromuscular relaxants to a patient. These drugs manage the patient's level of consciousness, pain management and neuromuscular blockade. Typically, each drug has a PK/PD model that specifies what the body does to the drug (PK) and how the drug interacts with the body (PD). These models are usually derived in isolation. In a clinical setting multiple drugs are typically used together.

Three-dimensional response surfaces have been developed to represent the interaction between two drugs. These surfaces represent the probability of non-response to a specific effect at different concentrations of the two drugs. This can also be considered an interaction (or synergistic) PD model. The challenge is to display these varying probabilities on a 2d graph that can easily be interpreted by a clinician during anesthesia.

The issue is confounded even more when there is more than one effect to display on the same graph. For example, when considering analgesia, one can consider varying levels of pain such as high pain, such as that experienced in intubation, and low pain, such as that experienced in post-operative analgesia. The challenge is to display these related but distinct surfaces on the same two-dimensional graph. The display should consist of the effect site concentration of the analgesic drugs which is at least one input to the 3d surface. The probability of each displayed effect, and reference points to those effects (such as 50% to 95% probability.)

Furthermore, typical anesthesia practice involves various combinations of drugs, which may not be fully supported by the response surface model. For example, a typical case may start with a propofol-remifentanil induction, and then proceed with isoflurane and remifentanil. Interactions between Propofol, isoflurane and remifentanil are not fully known at this time. Furthermore, use of antagonists—drugs that reverse the effects of other drugs—invalidate the primary drug's pharmacokinetic properties and need to be accounted for in the display.

SUMMARY OF THE DISCLOSURE

The system and method includes a treatment device such as an anesthetic machine or IV, a monitor and a display configured to display real-time PK/PD data associated with an anesthetic agent administered to the patient. The system and method further includes a safety control means configured to control the display such that one of a basic display state, an interactive effects display state, and a display inhibited state is selected and displayed according to the anesthetic agents and levels of the same being administered to the patient.

One aspect of the present disclosure is a system for safely displaying a pharmacokinetic/pharmacodynamics (PK/PD) drug model for a patient, the system comprising a treatment device for providing an anesthetic agent to the patient, a display for displaying real-time data associated with the quantity of anesthetic agent provided to the patient, wherein the display is configured to display the real-time data in any one of a plurality of formats including a basic display format, an interactive display format and a display inhibited format, and a safety control means adapted to control the formats of the display based on the anesthetic agent provided to the patient. The basic display format of the system is a default format. When the system does not have a model for the administered anesthetic agent the safety control means instructs the display to utilize the basic display format, when the administered anesthetic agent has a PK/PD model, and is above a predetermined minimum threshold, the safety control means instructs the display to utilize the basic display format. When a plurality of anesthetic agents are provided to the patient, and all of the plurality of anesthetic agents have a compatible interactive model, the safety control means instructs the display to utilize the interactive display format. When the interactive display format is being utilized and further wherein when an additional anesthetic agent is administered and the system does not have a model for the additional anesthetic agent the safety control means instructs the display to utilize the basic display format. When the administered anesthetic agent is an antagonist, the safety control means instructs the display to utilize a display inhibited format. The system further comprises a monitor configured to detect the quantity of anesthetic agent administered to the patient when the anesthetic is a gaseous anesthetic agent, an IV pump configured to send the quantity of anesthetic agent to the display, and an input device configured such that a user may enter the quantity of anesthetic agent into the display.

Another aspect of the present disclosure is a method of safely displaying a pharmacokinetic/pharmacodynamics (PK/PD) drug model for a patient, the method comprising providing an anesthetic agent to the patient with a treatment device, displaying real-time data associated with the quantity of anesthetic agent provided to the patient with a display, wherein the display is configured to display the real-time data in any one of a plurality of formats including a basic display format, an interactive display format and a display inhibited format, and adapted to control the formats of the display based on the anesthetic agent provided to the patient with a safety control means. The method comprises instructing the display to utilize the basic display format when the administered anesthetic agent has a none model with the safety control means, instructing the display to utilize the basic display format when the administered anesthetic agent has a PK/PD model, and is above a predetermined minimum threshold with the safety control means and instructing the display to utilize the interactive display format when a plurality of anesthetic agents are provided to the patient, and all of the plurality of anesthetic agents have a compatible interactive model with the safety control means. The method further comprises instructing the display to utilize the basic display format when the interactive display format is being utilized, and further wherein when an additional anesthetic agent is administered and the additional anesthetic agent has a none model with the safety control means, instructing the display to utilize a display inhibited format when the administered anesthetic agent has antagonistic model with the safety control means and detecting the quantity of anesthetic agent administered to the patient when the anesthetic is a gaseous anesthetic agent with a monitor. The method also comprises sending the quantity of anesthetic agent to the display with an IV pump, and entering the quantity of anesthetic agent into the display with an input device.

DETAILED DESCRIPTION OF THE DISCLOSURE

Figure 1:
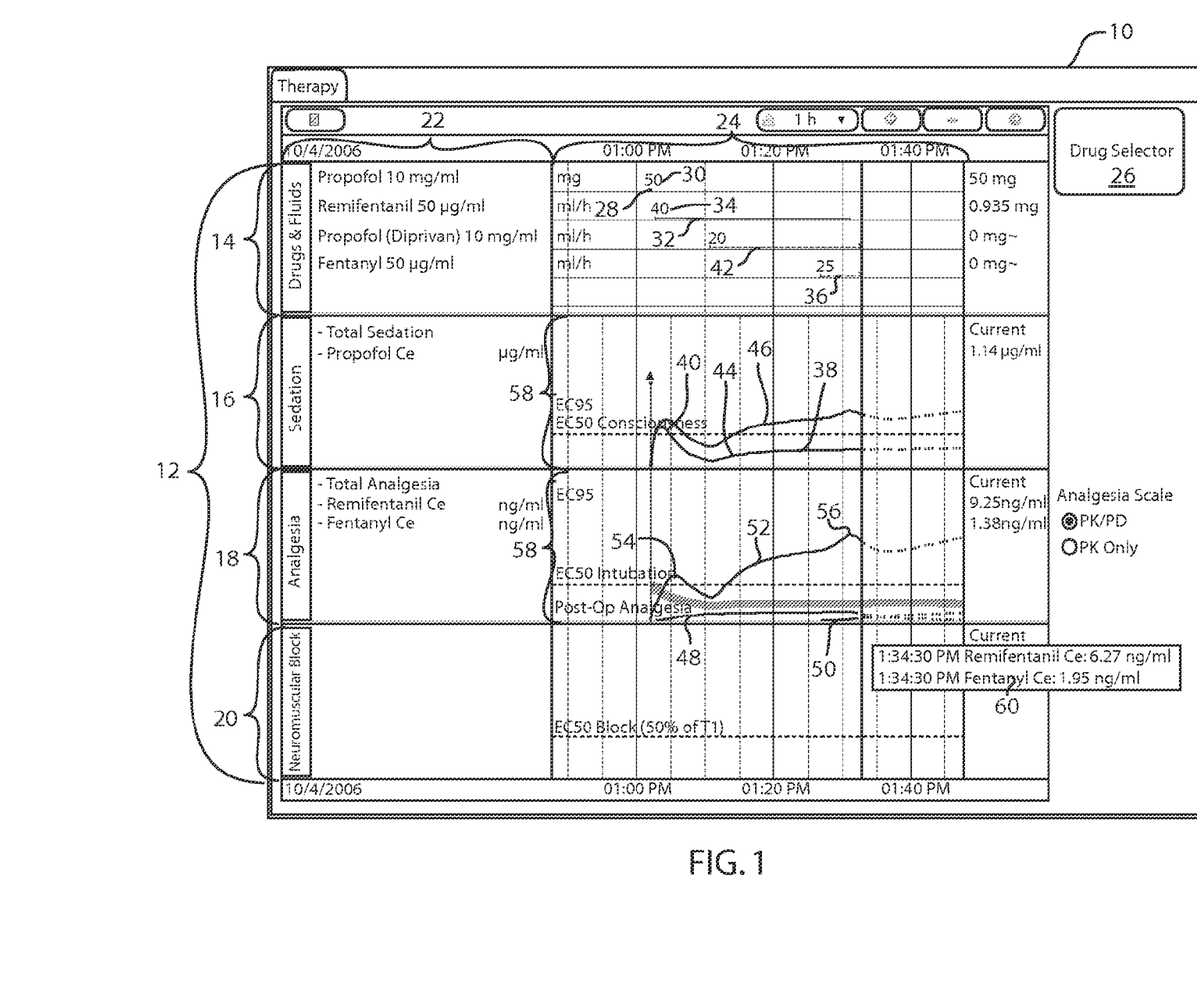
FIG. 1 is a screenshot of an embodiment of the system.

FIG. 1 depicts an embodiment of a user interface 10 for displaying drug administration documentation data and graphs based on the pharmacokinetic (PK) models and the pharmacodynamic (PD) models of the administered drugs. The user interface 10 may be displayed by any display or display associated with a device that may be present in a close proximity to a clinician providing anesthetic agents to a patient. Such a display may be a terminal for a computer workstation and may comprise CRT or flat-screen technology. Furthermore, the display may be such that the clinician interacts with the user interface 10 using touch-screen technology that is activated by the clinician's finger or a stylus, or alternatively the clinician controls a cursor with a mouse, data knob, or a directional pad. The user interface 10 comprises a plurality of windows 12. Embodiments of the user interface 10 may include a drug administration window 14, a sedation window 16, an analgesia window 18, and a neuromuscular block window 20. Each of the windows may comprise two regions, a drug listing region 22 and a time-based graph region 24.

A clinician may enter drug administration data by selecting a drug selector button 26. Alternatively, the clinician may enter drug administration data by selecting the drug administration window 14. The drug selector button 26 may open a drug library (not depicted) that can be edited by the hospital to include the potential anesthetic drugs that could be administered to a patient. Also, the drug library may include the drug concentrations that are available. Many anesthetic drugs have been studied to develop pharmacokinetic and pharmacodynamic models for the drugs based on basic patient demographic information such as age, sex, height, and weight. The drug library may include an indication of which drugs in the library have associated PK and PD models. Anesthesia can be divided into three basic effects: sedation (patient consciousness), analgesia (patient pain blocking), and neuromuscular blocking (patient relaxation). Each of the drugs in the drug library has a defined primary anesthetic effect. However, it is understood that any of the drugs may have effects in the other areas of anesthetic effect besides the drug's primary effect.

Once a clinician has selected a drug administration to document, the clinician may be prompted to enter the amount of the drug that was administered and the time at which the drug was administered. Further, the clinician may indicate that the administration was in the form of an injected bolus or as an IV infusion. Alternatively, if the device that is displaying the user interface 10 is connected to an IV infusion pump (not depicted) and the devices are able to properly communicate with each other the user interface may obtain drug infusion data such as the infusion rate and the infusion start and stop times from the infusion pump.

The user interface 10 displays the drug administration data in the drug administration window 14. The name of the drug appears in a listing in the drug listing region 22 of the drug administration window 14. As the administration of additional drugs are documented, these drugs are added to the bottom of the list. In an embodiment of the user interface 10, if more drugs have been administered than there is room for the drug administration window 14 to display, a scroll bar (not depicted) may appear, allowing a clinician to scroll through all of the documented drug administrations.

Additional drug administration data associated to the drugs listed in the drug listing region 22 is displayed in the graph region 24 of the drug administration window 14. For example, the drug Propofol is listed in the drug listing region 22. The number next to the name Propofol, "10 mg/ml" identifies the concentration of Propofol delivered. In the graph region 24 a dot 28 indicates a bolus of Propofol was delivered at approximately 1:02 PM. A drug amount indicator 30 identifies that 50 mg of Propofol was delivered in the bolus. Alternatively, the drug Remifentanil is listed in the drug listing region 22 at a concentration of 50 ug/ml. In the graph region 24, a line 32 indicates that an infusion of Remifentanil was delivered at approximately 1:03 PM. A drug rate indicator 34 identifies that the infusion was at a rate of 40 ml/hour. The line 32 is a solid line, thus indicating that the infusion has been completed, in this case the infusion represented by line 32 ended at approximately 1:31 PM. A dotted line, such as line 36 indicates that an infusion is presently ongoing, as the infusion of the drug Fentanyl indicated by line 36.

An embodiment of the user interface 10 allows for the documentation of a drug administration retroactively. This means that the clinician is allowed to enter the time of a drug administration when documenting a drug administration rather than the drug administration being only recorded in real time when the clinician documents it. Furthermore, once a drug administration has been documented by the clinician, the clinician can edit the drug administration data to correct any mistakes in the documentation, or to update the information, such as recording when an infusion of a drug ends.

The user interface 10 displays the proper pharmacokinetic (PK) models and pharmacodynamic (PD) models for each of the drugs documented by the clinician appearing in the drug administration window 14. The pharmacokinetic models and the pharmacodynamic models are displayed on a graph separately from the drug administration window 14. In an embodiment of the user interface 10, the user interface 10 further comprises the sedation window 16, the analgesia window 18, and the neuromuscular block window 20. As previously stated, each drug is classified as to the primary anesthetic effect of the drug. This primary anesthetic effect determines which window the PK and PD models for each drug are depicted.

The sedation window 16 displays the PK graph based on the PK model for any drugs that have a primary anesthetic effect as a sedative. Propofol has a primary effect as a sedative; therefore, Propofol is listed in the drug listing region 22 of the sedation window 16. The Propofol PK graph 38, displaying the effect site concentration of Propofol, is then displayed in the graph region 24 of the sedation window 16. The Propofol PK graph 38 is affected by the amount of Propofol administered, the time the Propofol was administered, and the characteristics of the Pronofol PK model. Therefore, an initial spike 40 in the Propofol effect site concentration appears shortly after the administration of the 50 mg bolus 28, followed by decay until the initiation of the 20 ml/hr infusion of Propofol 42, which produces an increase 44 in the effect site concentration of Propofol.

The sedation window 16 also displays a sedation PD graph 46 based on a sedation PD model for any drugs that have an anesthetic effect as a sedative. The sedation PD graph 46 may include data from drugs that have also been delivered to the patient that are not a sedative in primary effect, but may still produce some sedative effect. As a result the sedation PD graph 46 is an indication of the total sedation of the patient.

The analgesia window 18 also displays the PK graphs based on the PK models for any drugs that have a primary anesthetic effect as an analgesic. In FIG. 1, both Remifentanil and Fentanyl have a primary effect as an analgesic, therefore the analgesia window 18 displays more than one PK graph simultaneously. Both a Remifentanil PK graph 48 and a Fentanyl PK graph 50 appear in the graph region 24 of the analgesia window 18.

The analgesia window 18 also displays an analgesia PD graph 52 based on an analgesia PD model for any drugs that have any anesthetic effect as an analgesic. Therefore, despite Propofol having a primary effect as a sedative, Propofol also produces or contributes to an analgesic effect, and as such, a spike 54 in the analgesia PD graph 52 appears coinciding with the initial introduction of the 50 mg bolus 28 of Propofol. Furthermore, the analgesia PD graph 52 represents the combined analgesic effect of all of the administered drugs, therefore another spike 56 appears when the infusion of Fentanyl 36 is administered to the patient.

The graph region 24 of both the sedation window 14 and the analgesia window 16 comprise a normalized scale 58. The normalized scale 58 represents the percentage of the population that experiences a sedation or analgesic effect at a particular sedation or analgesia level. The normalized scale 58 then marks the level at which 50% (EC50) and 95% (EC 95) of the population experience the sedation or analgesic effect. The normalized scales 58 for sedation and analgesia PD graphs are specific to the sedation and analgesia PD models respectively. Additionally, the PK graphs are normalized to the normalized scale 58 also. The PK graphs are normalized to the effect site concentration required for an administration of that drug only to achieve the same sedation or analgesia effect.

While FIG. 1 does not display any information in the neurological block window 20, a similar display of neuromuscular PK and PD graphs, as described for the sedation window 14 and the analgesia window 16 is contemplated and considered to be within the scope of the present invention.

An embodiment of the user interface 10 further comprises a detailed information pop-up 60. A clinician using the user interface 10 in association with a device or display comprising an input means such as touch-screen technology or a cursor that is controlled by an input means such as a mouse, data knob, directional pad, or a keyboard can activate the detailed information pop-up 60 by touching or placing the cursor over any portion of a PK graph. The detailed information pop-up 60 appears on the user interface 10 and comprises detailed information regarding one or more PK graphs. The detailed information pop-up may identify a drug and present timing data and effect site concentration data for that drug at that point in time. Alternatively, another detailed information pop-up (not depicted) may similarly operate to provide detailed information regarding the PD graphs or drug administration data in the drug administration window.

The detailed information pop-up 60 improves the user interface 10 by keeping the windows 12 simple and easy to interpret, but allowing the clinician to have access to more detailed information regarding a particular portion of a PK or PD graph or a drug administration. The detailed information pop-up 60 also provides a solution to the tendency of the normalized scale 58 to suppress the PK graph in relation to the scale. The clinician can use the detailed information pop-up 60 to receive a more precise reading of effect site concentration than received by visual inspection of the PK graph.

Figure 2:
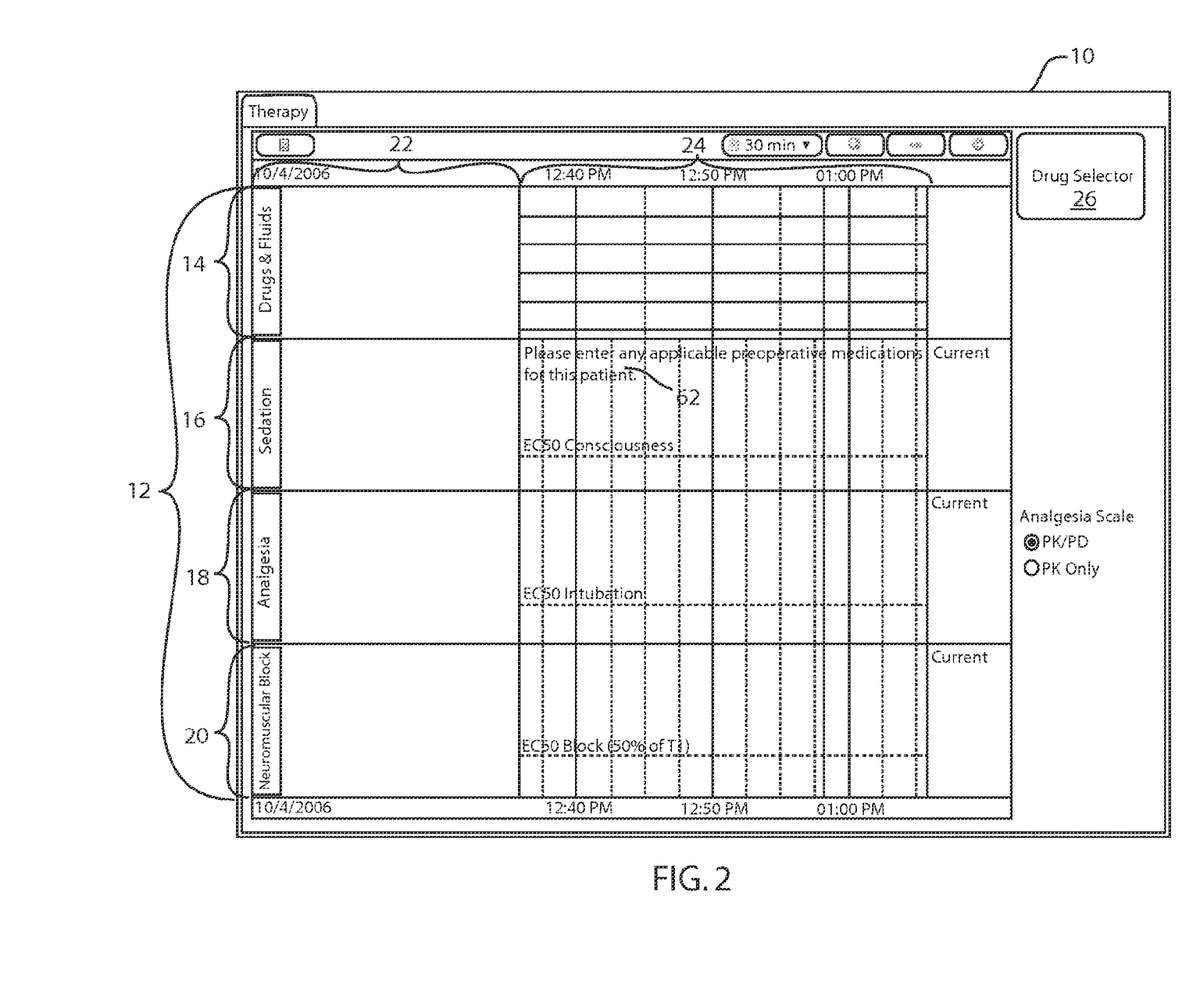
FIG. 2 is a screenshot of an embodiment of the user interface.

FIG. 2 depicts an embodiment of the user interface 10 as it may appear upon initialization of a program operating the user interface 10, before a clinician has documented the administration of any anesthetic drugs. The user interface 10 displays a pre-op warning message 62 located in the sedation window 16 that reminds the clinician to first enter into the user interface 10 any applicable preoperative medications that have already been administered to the patient. Alternatively, the pre-op warning message 62 may take the form of a text box or a textual message located in any of the other windows 12 of the user interface 10. This is an important safety feature because the clinician may forget to enter the preoperative medications that have been administered to the patient because the administration has already occurred. However, the presence of preoperative medications in the patient's body may have important effects on the PK or PD graphs for the drugs administered during the procedure.

Embodiments of the user interface 10 enhance the ease of use and understandability of the drug administration data and PK and PD graphs displayed on the user interface 10. A separated drug administration window 14 from the other windows displaying PK and PD graphs allows for the clinician to more easily track the documentation of drug administrations and provides the clinician with a clear record of what drugs were administered, when drugs were administered, how much drug was administered, and how the drug was administered.

Furthermore, the documentation of drug administration and the quality of the PK and PD models are improved in embodiments of the user interface 10. In embodiments of the user interface 10, the clinician is able to document the administration of drugs retroactively. This eliminates the need for an additional clinician to be present to perform the task of documenting the administration of drugs in real time, as required by user interfaces in the prior art. This has the added effect of helping to reduce the crowding that may be experienced in an operating room by reducing the number of people in the room by one. Additionally, if the clinician notices an error in the documentation of the administration of a drug, the clinician can edit the drug administration data to correct the error. The error correction ability improves the quality of the PK and PD graphs that are displayed as the PK and PD graphs are dependent upon the drug administration data.

Figure 3:
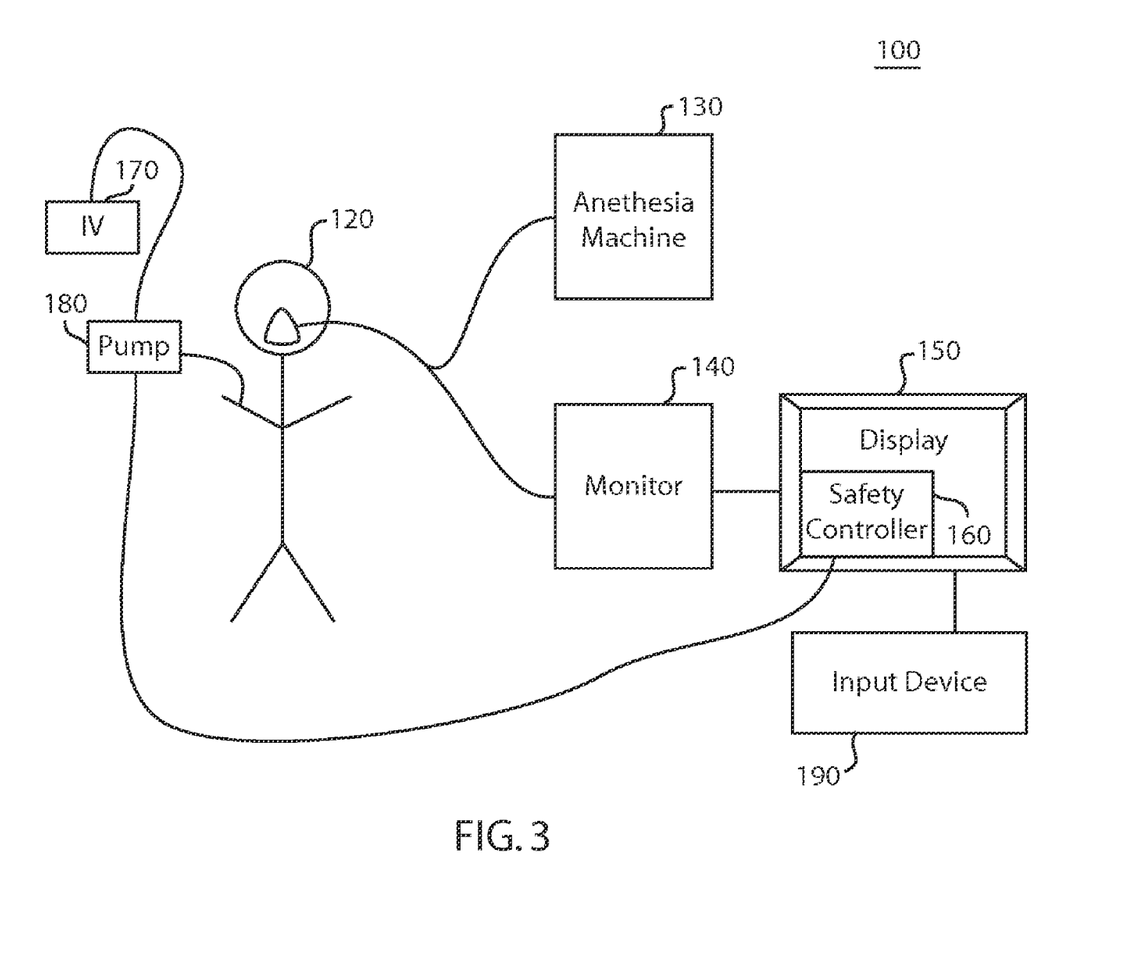
FIG. 3 illustrates a display system according to an embodiment of the present disclosure.

FIG. 3 illustrates a display system 100 according to an embodiment of the present disclosure. The aforementioned user interface is implemented in the display 150 of the display system 100. In the display system 100, a patient 120 receives anesthetic agent from an anesthesia machine 130 and/or an IV 170 and IV pump 180, while being monitored by a monitor 140. Such anesthetic agent administered by the anesthesia machine 130 includes inhaled, gaseous anesthetic, while a liquid anesthetic agent is administered by the IV 170 with the IV pump 180 or other known methods such as a bolus syringe (not shown). In one embodiment, the IV 170 and IV pump 180 are configured to notify the display 150 what anesthetic agent is being administered to the patient 120 with the IV 170 and IV pump 180. In other embodiments, an input device 190 is configured such that a user of the system 100 may enter the anesthetic agent being administered to the patient 120 with the IV 170 and IV pump 180.

Still referring to FIG. 3, the monitor 140 is any monitor known in the art that is configured to detect the quantities of any gaseous anesthetic agents administered to the patient 120 with the anesthesia machine 130. The monitor 140 sends the measured quantities of anesthetic agents to the display 150 such that the user interface (not shown) may display the levels for a physician or medical professional. A safety controller 160 is implemented to control the user interface on the display 150. In FIG. 3, the safety controller 160 is shown as included in the display 150. However, it should be noted that in other embodiments, the safety controller 160 may be implemented as part of the monitor 140, or as a separate piece of equipment. The safety controller 160 is configured to receive the quantity levels of the anesthetic agent in the patient 120 from the IV pump 18, input device 190, or monitor 140, and to adjust the user interface on the display 150 to one of any of the following displays: basic display; an interactive display; or a display inhibited. The safety controller 160 may utilize and execute a software program in order to effectuate such adjustment of the user interface on the display 150.

Figure 4:
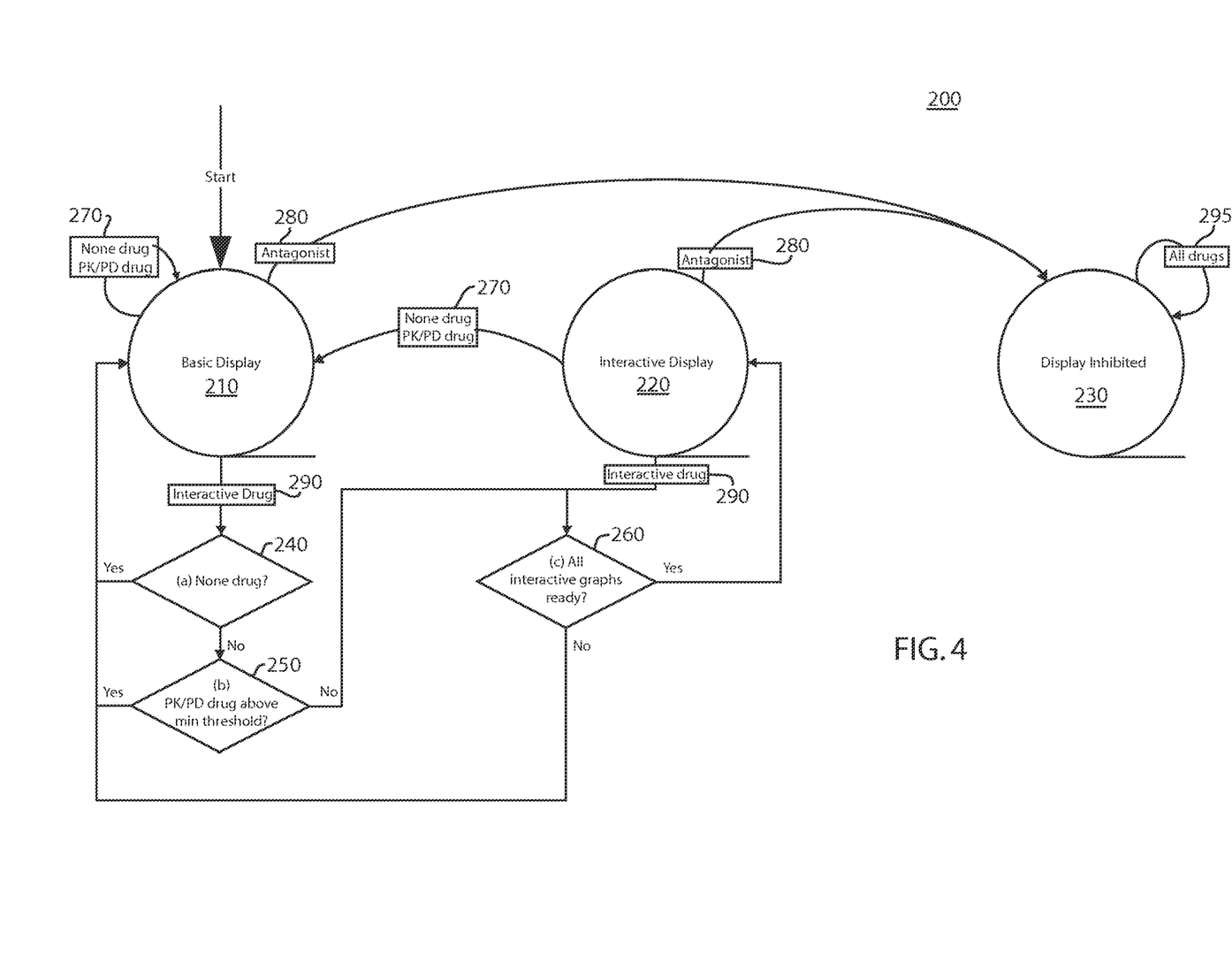
FIG. 4 illustrates a state transition diagram of a method according to an embodiment of the present disclosure.

FIG. 4 illustrates a state transition diagram of a display method 200 according to an embodiment of the present disclosure. Prior to executing the method 200, the drugs being administered to the patient are classified into four categories of models including: PK/PD models, interactive models, none models, and antagonist models. The PK/PD "pharmacokinetic/pharmacodynamic" models are models for drugs were effects of those drugs are known. Typically, the PK/PD model specifies what the body does to the drug and how the drug interacts with the body. The interactive models are displayed when the effects of combination of drugs are known. For example, if one specifically studied propofol and remifentanil together, propofol is a sedative and remifentanil is an analgesic, and when one administers the two drugs together, less of each one of the drugs is needed to experience either desired effect. The none model is displayed when no known models have been recorded for those drugs. Lastly, the antagonist model is displayed when drugs have an antagonistic effect on another drug. For example, when an administered drug actually reverses the effect of a first administered drug, the second drug would be considered antagonistic. The display method 200 starts by displaying a basic display 210 on the user interface. If a none drug or a PK/PD drug 270 is administered to the patient, the display continues in a basic display 210 mode. When an interactive drug 290 is administered to the patient it is first determined in step 240 whether there was a none drug previously administered, and if so, the display continues in a basic display 210 mode. If there was no prior none drug administered, then in step 250, it is determined whether there is a PK/PD drug above a minimum threshold, and if so, the display continues in a basic display 210 mode. If there is not a PK/PD above a minimum threshold, then it is determined in step 260 whether all the interactive graphs are ready. If so, then the display is reset to an interactive display 220 mode. If all of the interactive drug are not ready in step 260, then the display continues in basic display 210 mode.

Still referring to FIG. 4, when the display is in an interactive display 220 mode, and an additional interactive drug 290 is administered to the patient, the method continues back to step 260. When in the interactive display 220 mode, if a none drug or PK/PD drug 270 is administered to the patient, the display returns back to the basic display 210. Lastly, when the display is in either basic display 210 or interactive display 220 mode, and an antagonistic drug 280 is administered to the patient, the display is switched to a display inhibited 230 mode and all drugs administered thereafter 295 keep the display and the display inhibited 230 mode.

Figure 5:
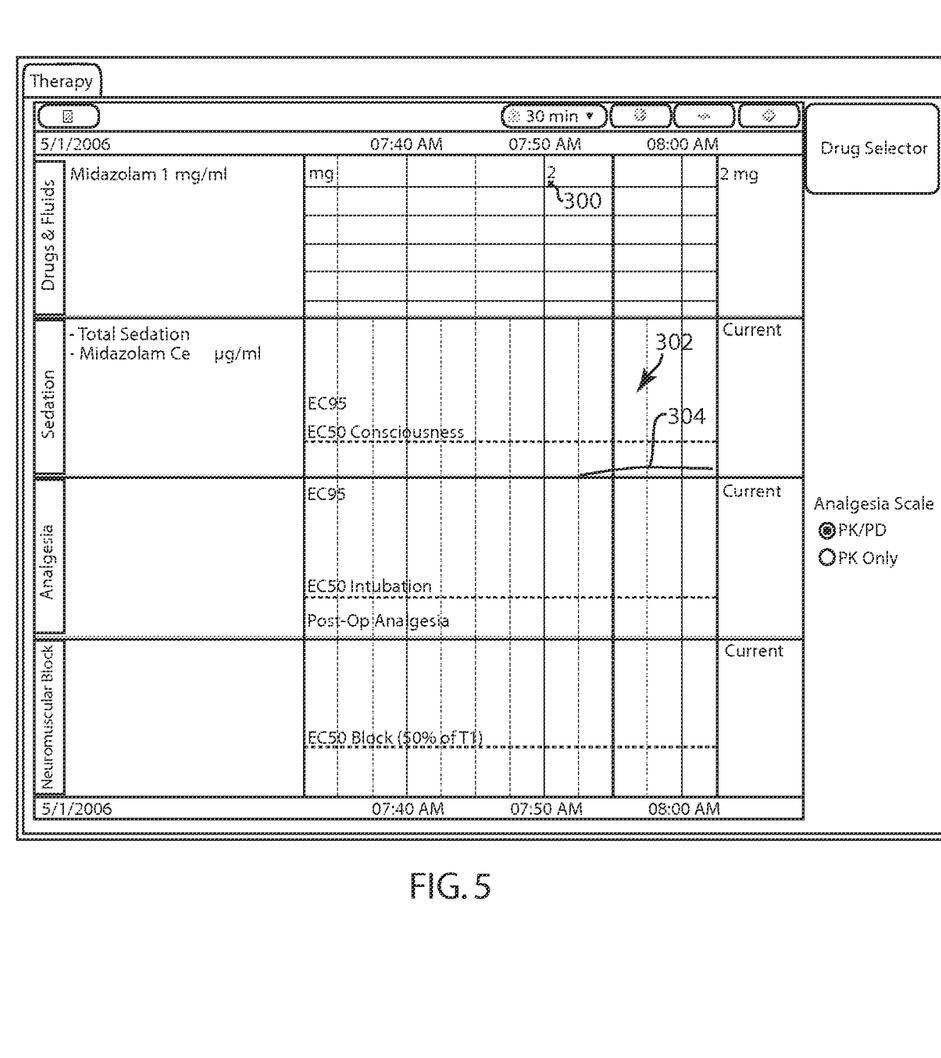
FIG. 5-7 are screenshots of examples of display modes according to an embodiment of the present disclosure.
Figure 6:
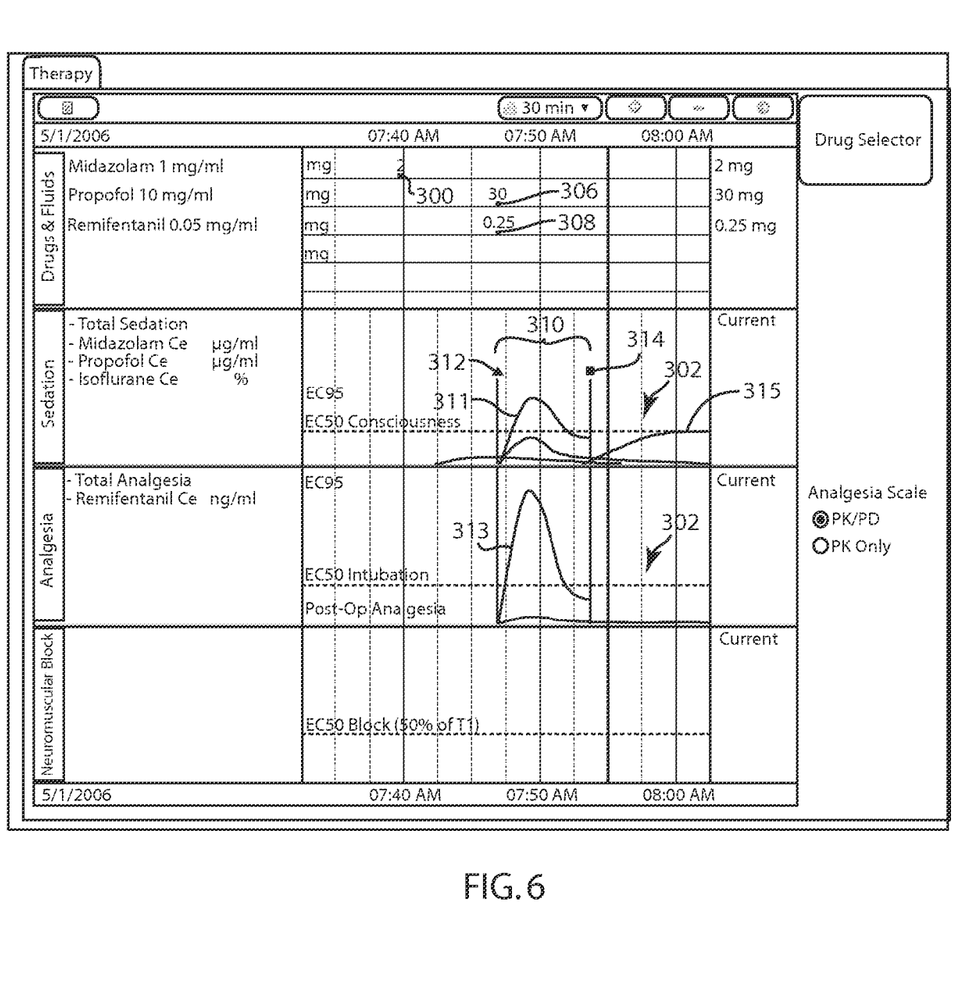
Figure 7:
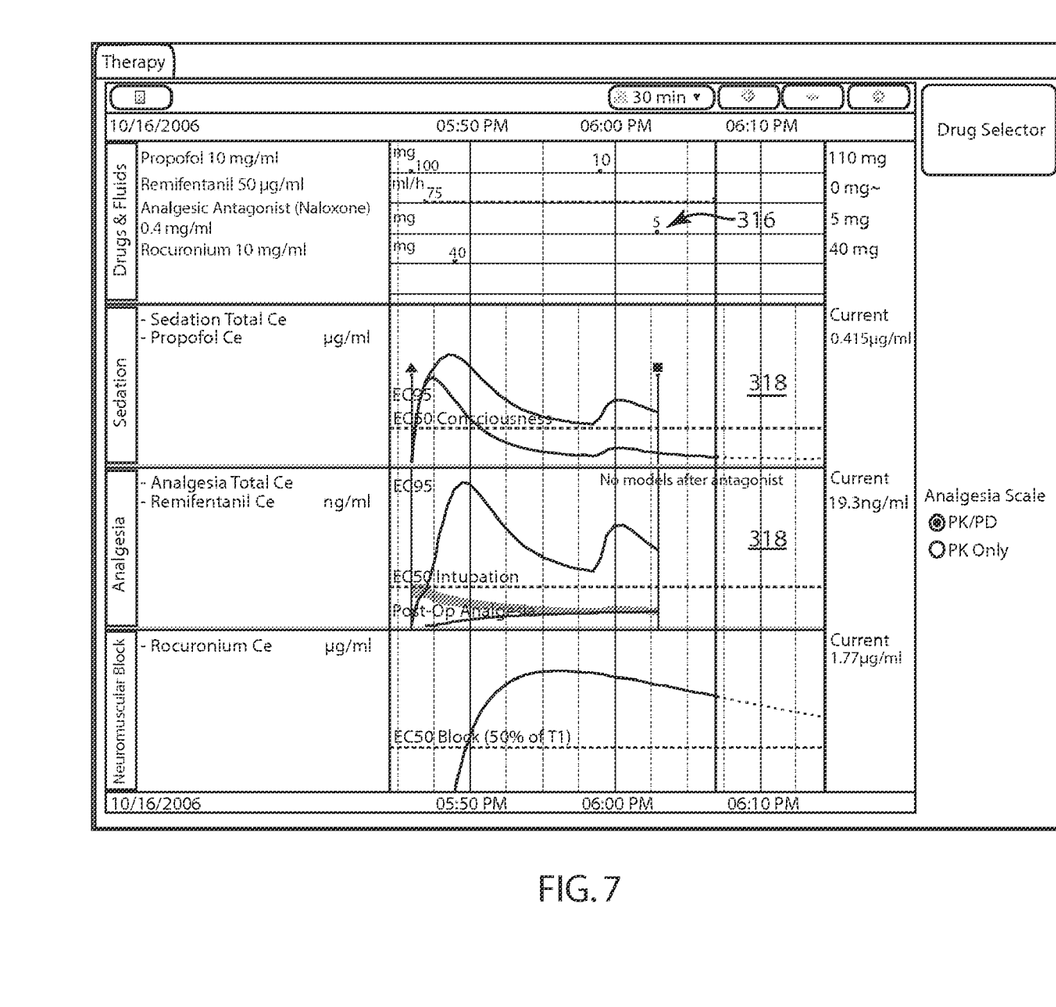

FIGS. 5-7 are screenshots that provide examples of each of the displays mentioned and described above. FIG. 5 displays an example of a basic display 302. In FIG. 5, the dot 300 represents a 2 mg does of Midazolam administered to a patient. Line 304 represents the PK/PD characteristics of the Midazolam over time, wherein no interactions from other drugs are currently present.

Referring now to FIG. 6, an interactions display 310 is depicted. Here, the dot 306 represents a 30 mg dose of Propofol given to a patient, as well as a 0.25 mg does of Remifentanil represented by dot 308. Because the three drugs listed are interactive drugs, an interactions valid 312 indicator starts the interactive display 310. In addition to the PK/PD characteristic graphs for each of the administered drugs, a total sedation characteristic curve 311 as well as a total analgesia characteristic curve 313 are present in the interactive display 310. The addition of the Isoflurane characteristic curve 315 puts the display back into the basic display 302 mode, and the interactive display 310 is ended by an interaction invalid 314 indicator.

Referring now to FIG. 7, a display inhibited mode 318 is depicted when a dose of an analgesic antagonist (naloxone) is administered to a patient, represented by the dot 316. Because the naloxone is an analgesic antagonist agent, the system and method places the user interface into display inhibited mode 318.

The present invention has been described in terms of specific embodiments incorporating details to facilitate the understanding of the principals of construction and operation of the invention. Such reference herein to specific embodiments and details thereof is not intended to limit the scope of the claims appended hereto. It will be apparent to those skilled in the art that modifications may be made in the embodiment chosen for illustration without departing from the spirit and scope of the invention.

What is claimed is:

1. A system for safely displaying a pharmacokinetic/pharmacodynamics (PK/PD) drug model for a patient, the system comprising:

a treatment device for providing an anesthetic agent to the patient;

a display for displaying real-time data associated with the quantity of anesthetic agent provided to the patient, wherein the display is configured to display the real-time data in any one of a plurality of formats including a basic display format, an interactive display format and a display inhibited format; and a safety controller adapted to control the formats of the display based on the anesthetic agent provided to the patient, wherein the basic display format is a default format, and further wherein when a plurality of anesthetic agents are provided to the patient, and all of the plurality of anesthetic agents have a compatible interactive model, the safety controller instructs the display to utilize the interactive display format, and further wherein when the administered anesthetic agent is an antagonist of any previously administered agent, the safety controller instructs the display to utilize a display inhibited format.

2. The system as claimed in claim 1, wherein when the system does not have a model for the administered anesthetic agent the safety controller instructs the display to utilize the basic display format.

3. The system as claimed in clam 1, wherein when the administered anesthetic agent has a PK/PD model, and is above a predetermined minimum threshold, the safety controller instructs the display to utilize the basic display format.

4. The system as claimed in claim 1, wherein when the interactive display format is being utilized, and further wherein when an additional anesthetic agent is administered and the system does not have a model for the additional anesthetic agent the safety controller instructs the display to utilize the basic display format.

5. The system as claimed in claim 1, further comprising a monitor configured to detect the quantity of anesthetic agent administered to the patient when the anesthetic is a gaseous anesthetic agent, and further configured to send the quantity of anesthetic agent to the safety controller.

6. The system as claimed in claim 1, further comprising an IV pump configured to send the quantity of anesthetic agent to the safety controller.

7. The system as claimed in claim 1, further comprising an input device configured such that a user may enter the quantity of anesthetic agent into the safety controller.

8. A method of safely displaying a pharmacokinetic/pharmacodynamics (PK/PD) drug model for a patient, the method comprising:
providing an anesthetic agent to the patient with a treatment device;
displaying real-time data associated with the quantity of anesthetic agent provided to the patient with a display, wherein the display is configured to display the real-time data in any one of a plurality of formats including a basic display format, an interactive display format and a display inhibited format; and
controlling the formats of the display based on the anesthetic agent provided to the patient with a safety controller, wherein the basic display format is a default format, and further comprising instructing the display to utilize the interactive display format when a plurality of anesthetic agents are provided to the patient, and all of the plurality of anesthetic agents have a compatible interactive model with the safety controller, and further comprising instructing the display to utilize a display inhibited format when the administered anesthetic agent has an antagonistic model with the safety controller, wherein the administered anesthetic agent is an antagonist of any previously administered agent.

9. The method as claimed in claim 8, further comprising instructing the display to utilize the basic display format when the administered anesthetic agent has a none model with the safety controller.

10. The method as claimed in clam 8, further comprising instructing the display to utilize the basic display format when the administered anesthetic agent has a PK/PD model, and is above a predetermined minimum threshold with the safety controller.

11. The method as claimed in claim 8, further comprising instructing the display to utilize the basic display format when the interactive display format is being utilized, and further wherein when an additional anesthetic agent is administered and the additional anesthetic agent has a none model with the safety controller.

12. The method as claimed in claim 8, further comprising detecting the quantity of anesthetic agent administered to the patient when the anesthetic is a gaseous anesthetic agent with a monitor, and sending the detected quantity to the safety controller.

13. The method as claimed in claim 8, further comprising sending the quantity of anesthetic agent to the safety controller with an IV pump.

14. The method as claimed in claim 8, further comprising entering the quantity of anesthetic agent into the safety controller with an input device.

* * * * *